United States Patent [19]

Taylor

[11] Patent Number: 5,045,205
[45] Date of Patent: Sep. 3, 1991

[54] REACTION VESSEL

[75] Inventor: John A. Taylor, Pinckney, Mich.

[73] Assignee: Separation Dynamics Inc., Southfield, Mich.

[21] Appl. No.: 472,085

[22] Filed: Jan. 30, 1990

[51] Int. Cl.$^5$ ............................................. B01D 61/24
[52] U.S. Cl. ..................................... 210/638; 210/490
[58] Field of Search ....................... 210/638, 632, 490; 427/213

[56] References Cited

U.S. PATENT DOCUMENTS

| | | | |
|---|---|---|---|
| 3,827,565 | 8/1974 | Matsumura | 210/321.75 |
| 4,361,484 | 11/1982 | Larsson et al. | 210/632 |
| 4,390,343 | 6/1983 | Walter | 436/518 |

Primary Examiner—Frank Spear
Attorney, Agent, or Firm—Reising, Ethington, Barnard, Perry & Milton

[57] ABSTRACT

A reaction vessel (10) includes a housing (12) having an interior cavity (14). Water insoluble reaction substances (16,16') are contained within the cavity (14) for producing a water soluble product from reacting with a water soluble precursor. A composite membrane defines at least a portion of the housing (12) for selectively imbibing the water soluble precursor therethrough into the housing (12) for reaction with the reaction substances (16,16'), imbibing of the product therethrough out of the housing (12) and being impermeable to the reaction substances (16,16') for maintaining the reaction substances (16,16') within the cavity.

14 Claims, 1 Drawing Sheet

U.S. Patent  Sep. 3, 1991  5,045,205
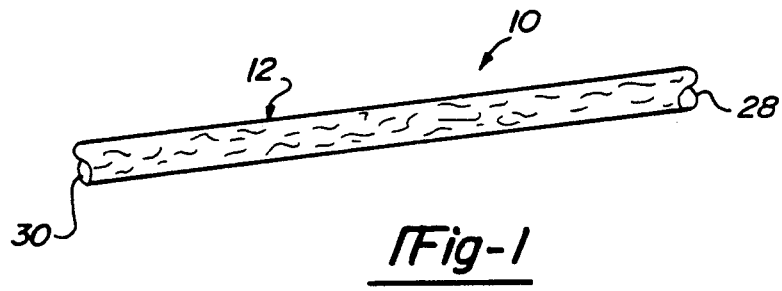
Fig-1
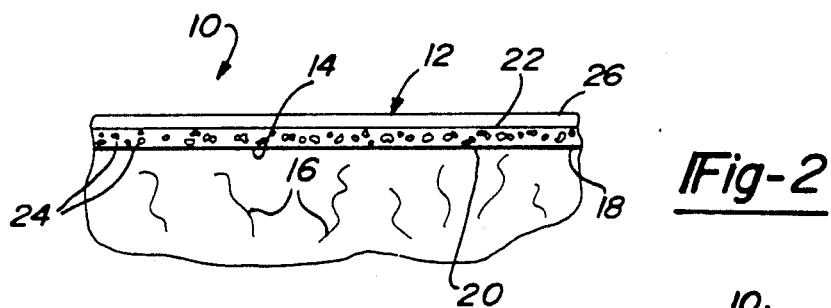
Fig-2
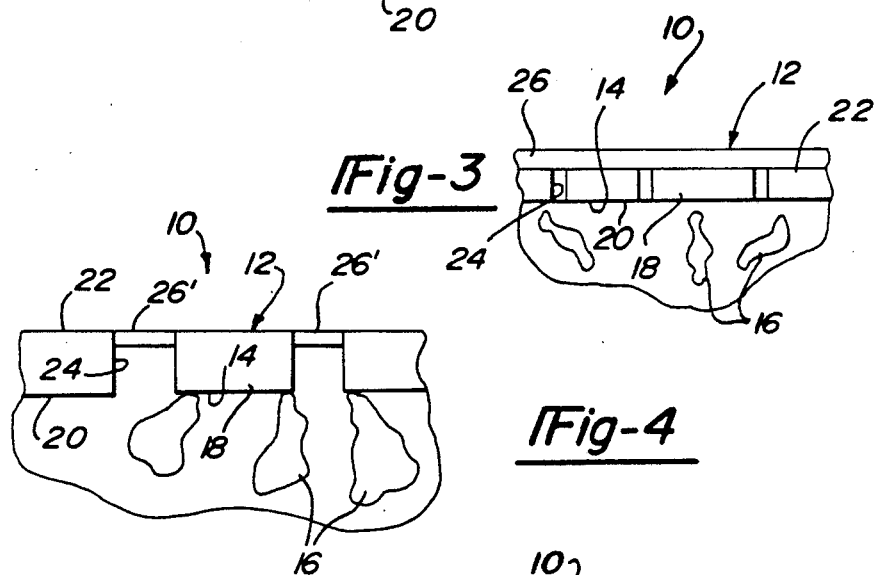
Fig-3
Fig-4
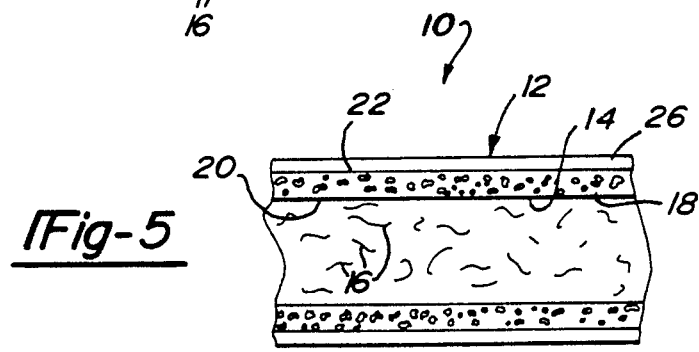
Fig-5

REACTION VESSEL

TECHNICAL FIELD

The present invention relates to membranes used for the separation of water and water soluble substances from relatively hydrophobic materials. More specifically, the present invention relates to a reaction vessel of the type which contains a reactor, such as an enzyme or cells which in the presence of a stimulator or precursor will generate and/or secrete a water soluble product which is transported out of the reaction vessel.

BACKGROUND ART

It is desirable in various organic environments to provide a reaction vessel which is not degraded in the organic environment and can interact with the organic environment to produce a product which is secreted or released back into the organic environment. For example, it is desirable in diabetic patients to be able to provide a means for producing insulin at a regulated rate in vivo. Other hormonal deficiencies could be treated by the implantation of a reaction vessel able to produce a hormone upon the proper stimulation by an organic stimulator from the hypothalamus. In constructing such a reaction vessel, a housing is required to retain the reactor. The housing must allow entrance of precursors or stimulators and allow the exit of the product made by the stimulated reactor. Further, the reaction vessel must inhibit reaction of itself or the product contained therein with the organic environment. The vessel must prevent degradation of itself and the reactor contained therein. For example, many prior art membranes are degraded in an organic environment.

The reaction vessel must prevent an immune reaction with either the vessel or the contents of the reactor contained therein. Further, the housing containing in the reactor must have structural integrity in the organic environment.

Functionally, the housing must allow passive transport therethrough of precursors or stimulators in one direction and product in the other.

The present invention provides a reaction chamber which is itself inert in an organic environment and further protects the reactor contained therein from the organic environment thereby preventing any immune reaction or enzymatic degradation of the reactor. The subject reaction vessel further allows transport therethrough of precursors and/or stimulants in one direction and product in the other.

SUMMARY OF THE INVENTION

In accordance with the present invention there is provided a reaction vessel including a housing having an interior cavity. Water insoluble reaction means contained within the cavity produces a water soluble product from reacting with a water soluble precursor or stimulator. Membrane means defines at least a portion of the housing for selectively imbibing the water soluble precursor or stimulator therethrough into the housing for reaction with the reaction means and imbibing of the product therethrough out of the housing. The membrane means is also impermeable to the reaction means for maintaining the reaction means within the cavity thereof.

FIGURES IN THE DRAWINGS

Other advantages of the present invention will be readily appreciated as the same becomes better understood by reference to the following detailed description when considered in connection with the accompanying drawings wherein:

FIG. 1 is a longitudinal view of a reaction vessel constructed in accordance with the present invention;

FIG. 2 is an enlarged fragmentary cross sectional view of the subject reaction vessel;

FIG. 3 is an enlarged cross sectional view of a second embodiment of the present invention;

FIG. 4 is a cross sectional view of a third embodiment of the present invention; and FIG. 5 is a cross sectional view of a fourth embodiment of the present invention.

DETAILED DESCRIPTION OF THE INVENTION

A reaction vessel constructed in accordance with the present invention is generally shown at 10 in the Figures. The reaction vessel 10 generally includes a housing, generally shown at 12. The housing 12 includes an interior cavity 14. The housing 12 contains nonwater soluble reaction means within the cavity 14 for producing a water soluble product from reacting with a water soluble precursor.

For example, the nonwater soluble reacting means could be cellular, such as pancreatic islet cells 16 shown in FIGS. 3, 4 and 5. If the nonwater soluble reaction means are islet cells 16, then the water soluble precursor is glucose and the water soluble product is insulin. Alternatively, the nonwater soluble reaction means could be an enzyme, as schematically shown in FIG. 2 at 16'. For example, if the enzyme is an isomerase, then the precursor or stimulator could be a dextro rotatory glucose molecule and the product could be a levo rotatory sugar molecule. The criticality for the water solubility of the product and precursor and nonwater solubility of the reaction means 16 is clarified below.

The reaction vessel 10 includes membrane means defining at least a portion of the housing 12 and preferably defining the housing 12 in its entirety. The membrane means selectively imbibes water soluble precursor therethrough in the direction into the housing 12 for reaction with the reaction means 16, imbibes the product therethrough in the opposite direction out of the housing 12 and is impermeable to the reaction means 16 for maintaining the reaction means 16 within the cavity 14

More specifically, the membrane means includes a porous inner support layer 18 having an inner side surface 20 and an outer side surface 22 and a plurality of pores 24 extending therethrough for providing communication between the two sides 20, 22. For example, the porous support 18 can be a microporous membrane material. The microporous membrane material can be selected from the group including but not limited to polypropylene, polyvinyldene fluoride, polytetraflouroethylene, polysulfone, polyamide, polyimide, microporous ceramics, and sintered metals. Each of these materials include micropores extending from one side thereof to the other side thereof. Microporous materials may be selected from those having pore sizes of less than 1 micron to materials of pore sizes of over 100 microns or greater as desired. The material provides a structural support for a nonporous layer to be described below.

The membrane means includes nonporous water and water soluble substance permeating means 26 as shown in FIGS. 2, 3 and 5 disposed over each of the pores 24 for selectively permeating only water and water soluble substances through each of the pores 24. As shown in FIGS. 2, 3 and 5, the nonporous water and water soluble substance permeating means 26 forms a second layer inert to degradation to organic materials as a second layer adhered to and completely covering the first layer 18 of microporous material. The nonporous water and water soluble substance permeating means 26 is a membrane made from regenerated cellulosic material, such as viscose or cuproammonium regenerated cellulose. By regenerated cellulose, it is meant that the cellulose used is a regenerated cellulose in its natural state. In other words, the cellulose molecules per se are not chemically altered. Cuproammonium regenerated cellulose is nonchemically derivatized cellulose in substantially its natural state. The cuproammonium regenerated cellulose is chemically sheets of cellulose molecules. The specific ultrastructure is not known but it is known that the sheets have no pores extending therethrough. There is heavy hydrogen bonding between the sheets creating a highly crystalline structure. This structure is quite hydrophilic and provides aqueous pathways for water and dissolved water soluble materials, such as the water soluble precursors or stimulators and the water soluble products. The water and dissolved water soluble materials are imbibed into the membrane and diffused therethrough. The cuproammonium regenerated cellulose provides membranes which are significantly thinner than membranes made by chemically derivatized cellulose materials, such as cellulose acetate.

Materials diffusing through the cuproammonium cellulose membranes travel a significantly smaller distance than materials traveling through cellulose acetate membranes. Thus, the cuproammonium cellulose membranes have a significant positive effect on the flow dynamics by presenting a significantly smaller yet more effective barrier over which the diffusing water and dissolved water soluble components pass. However, unlike prior art devices which include cuproammonium cellulose fibers which are unsupported, the porous support of the present invention allows the manufacturing of a second layer of nonporous cuproammonium cellulose thereover which is significantly thinner than those previously made and used unsupported cuproammonium fibers. Layers as thin as one micron or less of the nonporous cuproammonium cellulose can be adhered in the porous support layer and have a sufficient structural integrity to provide a fluid separation system. Such composite membranes are disclosed in the co-pending U.S. Pat. No. 402,229 to Taylor, the inventor the present invention, filed Sept. 5, 1989.

As shown in FIG. 4, the porous support layer 18 includes pores 24 having the cuproammonium cellulose material 26' solely within the pores 24. In this manner, ultra-thin layers or bubbles of cuproammonium cellulose can be adhered within the pores and function in accordance with the present invention. By making the pores smaller, the layer of cuproammonium cellulose can be made thinner to enhance and maximize the efficiency of the membrane since making the membrane thinner increases the flow rate of water and water soluble substances therethrough. The regenerated cellulose membrane, being nonporous, functions as a barrier to the passage of very small molecules, including microbes and antibodies, and is at the same time water permeable. Since water permeates by diffusion, the thinner regenerated cellulose membranes permit the flow of water faster than do thicker membranes of the similar type under the same conditions.

The cuproammonium cellulose outer layer, as shown in FIGS. 1, 2, 3 and 5 provides a significant advantage in biological systems. The cuproammonium cellulose or viscous layer is inert in hostile biological environments. The regenerated cellulosic layer does not initiate an immune response in a biological system, nor is it degraded by organic or enzymatic materials in the environment. Further, the regenerated cellulose nonporous layer prevents the ingress of antibodies, enzymes or other substances which could attack and degrade the reactor means contained within the housing 12. Coincidentally, the reactor material, such as molecules as small as enzymes, are trapped and maintained within the housing 12 as these materials are prevented from passing through the pores 24 by the nonporous regenerated cellulosic membranes 26,26'. In this manner, the present invention provides a completely inert vessel or carrier for a bioreactant which can be stimulated by environmental precursors or stimulators and can produce a product which is released from the reactor while the reacting material is isolated from the environment. Of course, the reaction vessel can be placed in other environments where enzymatic degradation or immune reaction is not critical. Thusly, the embodiment of FIG. 4 where the microporous material per se is exposed to the environment, can be utilized.

As stated above, the reaction means 16,16' can include an enzyme 16' suspended in a fluid within the cavity 14, as shown in FIG. 2, of the type for reacting with a water soluble precursor to derive a water soluble product. As discussed above various isomerases, reductaces or other enzymes which themselves are not water soluble but react with water soluble precursors or stimulants to produce a water soluble product may be utilized with the present invention. Alternatively, the enzyme 16' can be fixed to the microporous inner membrane layer 18 by techniques well known in the art. Examples of such techniques are disclosed in detail in IMMOBILIZED ENZYMES, PREPARATION AND ENGINEERING, Johnson, J. C., 1979, Noyes Data Corp., publisher. It is critical that the fixing technique not critically alter the activity of the enzyme.

As discussed above, the reactor means 16 can consist of insulin producing cells such as porcine islet cells 16 for actively taking up and reacting with glucose and producing insulin. The islet cells 16 can be fixed or nested among the pores 24 by techniques well known in the art for fixing cells to microporous membranes or the cells can be free and contained within the housing 12, as shown in FIG. 5. For example, the ends of the housing can be sealed in order to permanently retain the porcine islet cells. The housing containing active islet cells then may be implanted in vivo. Water, containing nutrients including glucose will defuse into the housing, while insulin produced by the porcine islet cells and metabolites will defuse out of the housing. However, foreign body reaction is prevented because no contact of leucocytes or antibodies with the porcine islet cells is possible. Because the nonporous membrane layer is impermeable to antibodies and antibody producing cells immune rejection of the porcine islet cells prevented.

As shown in FIG. 1, a reaction vessel made in accordance with the present invention can be formed from a hollow fiber bilayer made in accordance with the invention disclosed in the previously cited copending application Ser. No. 402,229 to Taylor, filed Sept. 5, 1989, now U.S. Pat. No. 4,978,451. The reacting means, such as the bovine islet cells 16 or enzyme 16' can be loaded into the cavity 14 and the ends 28,30 of the fiber can be closed. For example, if the microporous material used to make the inner layer 18 is a thermoplastic, then the ends of the housing 12 can be heat sealed by a heat sealer known in the art. Other materials, such as Teflons can be sealed with a cyanoacrylate. Various other means known in the art can be used to seal the ends of fibers made from various other microporous materials.

The microporosity of the inner layer 18 can be chosen depending on the various features needed.

The present invention further provides a method of producing water soluble product from water insoluble precursors or stimulators, the method generally including the steps of housing the water soluble reaction substance 16,16' capable of producing the water soluble product from reacting with the water soluble precursor in the cavity 14 of the housing 12, selectively imbibing the water soluble precursor or stimulator through the membrane portion of the housing 12 into the cavity 14 for reaction with the reaction substance 16,16' and selectively imbibing the water soluble product through the membrane out of the housing 12. In the meantime, the membrane maintains the reaction substance 16,16' within the cavity 14.

The cells 16 or enzymes 16' or other reaction material can be maintained in a fluid environment within the housing 12. For example, living cells can be maintained in any appropriate nutrient medium such as Ringers solution. Similarly, enzymes can be maintained in various solutions, which maximize their activity and longevity.

Thusly, the present invention provides a reaction vessel capable of maintaining its integrity in organic and biological systems and capable of producing water soluble products in the presence of or being stimulated by water soluble precursors or stimulators in the organic system. For example, a reaction vessel 10 made in accordance with the present invention and containing bovine islets cells can be implanted in proximity of a vascular supply. The reaction vessel 10 would be stimulated by blood glucose levels to either produce or not produce insulin so as to supplement a diabetic patient with insulin. If the embodiment shown in FIGS. 1, 2, 3 or 5 is used, the reactor would be inert to enzymatic or other biological degradation, would not produce an immune response as the cellulosic nonporous outer layer would not activate the immune system, and the reaction vessel 10 would isolate the bovine islet cells from the outer environment. Accordingly, the bovine islet cells themselves would not elicit an immune response or be susceptible to degradation.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed:

1. A reaction vessel (10) comprising: a housing (12) including an interior cavity (14); water insoluble reaction means (16,16') contained within said cavity (14) for producing a water soluble product from reacting with a water soluble precursor; and membrane means defining at least a portion of said housing (12) for selectively imbibing the water soluble precursor therethrough in said housing (12) for reaction with said reaction means (16,16'), imbibing of the product therethrough out of said housing (12), and being impermeable to said reaction means (16,16') for maintaining said reaction means (16,16') within said cavity (14). Said membrane means including a porous support (22) having a plurality of pores (24) extending therethrough and a nonporous water and water soluble substance permeating membrane (26) supported by said porous support (22) over each of said pores (24).

2. A vessel as set forth in claim 1 wherein said nonporous water and water soluble substance permeating means (26) forms a second layer inert to degradation by organic materials as a second layer adhered to and completely covering said first layer (18).

3. A vessel as set forth in claim 2 wherein said nonporous water and water soluble substance permeating means (26) comprises viscous or cuproammonium regenerated cellulose.

4. A vessel as set forth in claim 1 wherein said housing (12) consists of said membrane means defining said interior chamber (14) surrounded by said porous inner support (18) and said second layer (26.26').

5. A vessel as set forth in claim 1 wherein said porous support means (18) consists of a microporous material.

6. A vessel as set forth in claim 1 wherein said reaction means (16,16') includes an enzyme (16') suspended in a fluid within said cavity (14) of the type for reacting with a water soluble precursor to derive a water soluble product.

7. A vessel as set forth in claim 6 wherein said enzyme (16') is glucose isomerase.

8. A vessel as set forth in claim 6 wherein said enzyme (16') is fixed to said microporous inner membrane layer (18).

9. A vessel as set forth in claim 1 wherein said reaction means (16) are bovine islet cells (16) for actively taking up and reacting with glucose and producing insulin.

10. A vessel as set forth in claim 9 wherein said islet cells are nested in said pores (24) of said inner microporous membrane layer (18).

11. A method of producing a water soluble product from a water soluble precursor, said method including the steps of: housing a water insoluble reaction substance (16,16') capable of producing a water soluble product from reacting with a water soluble precursor in a cavity (14) of a housing (12); selectively imbibing the water soluble precursor through a membrane portion of the housing (12) into the cavity (14) for reaction with the reaction substance (16,16'), said membrane portion including a porous support (22) having a plurality of pores (24) extending therethrough and a nonporous water and water soluble substance permeating membrane (26) supported by said porous support (22) over each of said pores (24) selectively imbibing the water soluble product through the membrane out of the (11) housing (12); and maintaining the reaction substance (16,16') within the cavity (14) and from imbibing through the membrane.

12. A method as set forth in claim 11 wherein the reaction substance (16,16') is cellular (16') and the membrane including a porous inner layer (18) and a nonporous hydrophilic outerlayer (26) at least over the pores (24) of the inner layer (18), said housing step being further defined as nesting the cells (16) in the pores (24) of the porous inner layer (18).

13. A method as set forth in claim 11 wherein said housing step is further defined as suspending the reaction substance (16,16') in a fluid medium within the cavity (14).

14. A method as set forth in claim 13 wherein the housing (12) includes an inner wall defining the cavity (14), the housing step being further defined as fixing the reaction substance (16,16') to the innerwall while maintaining the capacity of the reaction substance (16,16') to form product in the presence of precursor.

* * * * *